(12) United States Patent
alSafadi et al.

(10) Patent No.: US 8,219,608 B2
(45) Date of Patent: Jul. 10, 2012

(54) SCALABLE ARCHITECTURE FOR WEB SERVICES

(75) Inventors: Yasser alSafadi, Yorktown Heights, NY (US); Amr F. Yassin, Ossining, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 2535 days.

(21) Appl. No.: 10/176,237

(22) Filed: Jun. 20, 2002

(65) Prior Publication Data
US 2003/0236824 A1 Dec. 25, 2003

(51) Int. Cl.
G06F 15/16 (2006.01)
(52) U.S. Cl. ........................................ 709/203
(58) Field of Classification Search .................. 709/203
See application file for complete search history.

(56) References Cited

U.S. PATENT DOCUMENTS

| | | | | |
|---|---|---|---|---|
| 5,153,906 | A * | 10/1992 | Akiyama | 379/114.15 |
| 5,555,244 | A | 9/1996 | Gupta et al. | 370/60.1 |
| 5,781,724 | A | 7/1998 | Nevarez et al. | 395/186 |
| 6,691,914 | B2 * | 2/2004 | Isherwood et al. | 235/375 |
| 6,731,238 | B2 * | 5/2004 | Johnson | 342/357.09 |
| 6,741,853 | B1 * | 5/2004 | Jiang et al. | 455/418 |
| 2003/0055868 | A1 * | 3/2003 | Fletcher et al. | 709/201 |
| 2004/0176958 | A1 * | 9/2004 | Salmenkaita et al. | 704/275 |

FOREIGN PATENT DOCUMENTS

| | | |
|---|---|---|
| JP | 08315200 | 11/1996 |
| JP | 09115021 | 5/1997 |
| JP | 00259802 | 9/2000 |
| JP | 00259968 | 9/2000 |
| JP | 00293642 | 10/2000 |
| SE | 9800761 | 10/1999 |

OTHER PUBLICATIONS

Zhao, Y. "WebEntree: A Web Service Aggregator." 1998. IBM Systems Journal, IBM Corp. pp. 584-595.*
"A Novel Architecture for Active Service Management", by I.W. Marshall, H. Gharib, J. Hardwicke and C. Roadknight, DSOM2000.
Y Zhao, "WEBENTREE: A Web Service Aggregator", IBM Systems Journal, IBM Corp., Armonk, NY, vol. 37, No. 4, 1998, pp. 584-595, XP0001002913, pp. 586-587, Section "Architecture", pp. 591-592, section "WebEntree" pp. 594, subsection "Service management".
Shaohua, "Fast Control in Object-Oriented Repetitive Access", Security Technology, 1993, Security Technology, Proceedings, Institute of Electrical and Electronic Engineers 1993, International Carnahan Conference on Ottawa, Ont., Canada, Oct. 1993, New York, NY, Oct. 1994, pp. 173-175, XP010146509.

* cited by examiner

*Primary Examiner* — Larry Donaghue
*Assistant Examiner* — Nicholas Taylor (57) ABSTRACT

System and method for providing a customized service in a network. The system comprises at least one originating device that provides an identifier of one of a user and a product associated with the user (Tag ID) and an identifier of the customized service (Object ID). It further includes a processor that supports an action table. The processor receives the Tag ID and Object ID from the at least one originating device, and uses at least the received Tag ID and Object ID to look up a corresponding action in the action table. A servicing node in the system receives the action and performs at least partial execution of the action, thereby generating results comprising the customized service.

15 Claims, 5 Drawing Sheets

SCALABLE ARCHITECTURE FOR WEB SERVICES

FIELD OF THE INVENTION

The invention relates to network architecture, scaling of network architecture and routing of requests for network services.

BACKGROUND OF THE INVENTION

Current network services, including Internet services, generally require that a user directly invoke the service. Once the service is invoked, the invoked service is responsible for fulfilling the request. For example, on the Internet, a person invokes a service by submitting a request via his or her PC. The invoked service fulfills the request.

As a specific example, a person may order the latest book "Tishimingo Blues" by Elmore Leonard using the well-known Amazon.com website. The user clicks on a series of icons in the Amazon website corresponding to the title and then checks out by entering various shipping and payment information, thus submitting the order. Once submitted to Amazon, the order is processed by Amazon and the book is shipped to the person.

In some cases, a network service node may create and maintain a database that automatically returns results to a person that access the node. For example, many websites create preferences based on a person's prior purchases or queries. Software "cookies" are stored on the person's PC, and automatically transmitted to the website when the person accesses the website. The cookies identify the terminal (and by surrogate, the person) to the service node, the preferences for the person are retrieved by the service node from the database, and purchasing suggestions are made to the person based on the preferences. The preferences tendered, however, are routinely developed and proffered by the website entity itself based on its own commercial goals. They are not, for example, formulated and proffered in response to the device used to invoke the website, or tailored to a service invoked by the user.

There are a number of disadvantages with this arrangement. One principle disadvantage is that the user invokes and thus selects the service node to service his or her request. However, this requires that the user know how to formulate a request, navigate the network and find a servicing node. The servicing node that the user finds, however, may not be the optimum provider. For example, a user living in Europe may invoke a website in Wyoming to service the request, thus incurring additional shipping costs and delays, when there is a local alternative that could have serviced the request faster and cheaper.

Another disadvantage of direct invocation of a network servicing node by users, and the servicing of those requests by the service node, is that the service node can be overwhelmed by user requests. This can lead to delays in servicing the request. This is particularly disadvantageous when another servicing node might be immediately available to provide an equivalent service to the excess users.

Another disadvantage of direct invocation of a network servicing node by users is that a person must recognize that he or she needs the service and actively access the servicing node by formulating and manually entering a request. If, for example, a user is about to put a silk shirt from the Gap into a washing machine at the wrong temperature, but does not realize it, it makes no difference that the Gap website may include washing instructions for its products. Even in the case of the servicing node that automatically provides preferences to the user who access the servicing website, the user must first access the website and, even then, the preferences that are returned by the website are developed by the website and may have nothing to do with the user's current needs.

A local network has certain analogous features and disadvantages. For example, a work facility may have card readers at each entrance that are connected to a facility server. When a worker swipes his or her ID at one of the readers (thus identifying himself or herself to the system), a database is consulted to determine that the person is currently employed. If so, the server returns a signal to open the door latch corresponding to the reader. Again, the person directly invokes the service by providing the ID to the card reader, and the invoked service provides the result (a door unlock command).

Continuing the local network example, more than one parameter apart from the person's ID may be submitted to the server in the service request. For example, the facility may have a number of secure rooms to which access is restricted to certain employees. When a person swipes an ID at a particular reader, the person's ID and the reader location (two parameters) is used to look up in the database whether the particular person is allowed access to the room corresponding to the reader. If so, the server sends an unlock command. If not, then the door remains locked.

Additional parameters may be considered with the service request. For example, the server may also consider other parameters in determining whether to allow the person access to the room. For example, if the database reflects that the person works normal business hours and he is swiping his ID at a reader for a secure room at 1 a.m., then the door may remain locked.

Even in a local network environment as described, the user must be aware of the service and actively invoke the service. The database relied on is dedicated to a particular function, such as unlocking an entrance and does not accommodate other devices. The network server may also be overwhelmed if multiple users invoke the service simultaneously. Even if there are multiple servers that can accommodate excess service requests, the routing of requests may not be invoked in the most efficient manner.

SUMMARY OF THE INVENTION

It is thus an objective of the invention to provide a network architecture that provides for automatic generation and transmission of sensor-read or system parameters, including those input by the user, which form the basis of a request. It is also an objective of the invention to provide a network architecture that automatically receives such parameters, processes the parameters into corresponding action requests, and routes the action request to an appropriate network node for servicing the action. It is also an objective of the invention that, when appropriate, the request is routed to invoke a plurality of services or service providers for servicing the request.

It is also an objective of the invention that the network architecture of the invention be scalable, to avoid delays when multiple action requests are generated by multiple user input parameters. Thus, it is an objective that the network architecture allow for alternate routing in the network to alternative servicing nodes that can service the action request. It is also an objective that the network architecture be expandable to include new or duplicate service nodes, and that the network architecture of the invention be capable of being mapped on to many different network topologies, from local networks to the large scale networks, such as the Internet.

Accordingly, the invention provides a system and method for generating and processing requests over a network. One or more parameters that form the basis for a request are generated at a user end. The parameters comprise a tag identification (Tag ID) and an object identifier (Object ID). The Tag ID may be an identification associated with a user/person or it may be a identification associated with a product. A Tag ID may be included in a physical item, such as a magnetic strip embedded in the product or a magnetic strip on a person's ID card. The Tag ID may also be a non-physical identification, such as a serial number, product ID, user ID, etc associated with a person or product. The Object ID may be an identifier for any device, system or service which is invoked.

The Tag ID, Object ID and any other parameters are transmitted from the user node to a network node that hosts an action table, look-up table, database, or the like. (Because of its descriptive nature, "action table" will be used hereinafter.) The transmitted parameters are used to look up a corresponding operation or action (referred to hereinafter as an "action") on the action table.

The action corresponding to the parameters in the action table may also be executed in whole or in part at the node that hosts the action table. Alternatively, the action may designate a servicing node in the network for servicing the action. The action is transmitted to the designated servicing node, where the action is executed and results are generated and processed.

The invention also comprises a system for providing a customized service for a user in a network. The system comprises at least one originating device that provides an identifier of one of a user and a product associated with the user (Tag ID) and an identifier of the customized service (Object ID). It further includes a processor that has an associated action table. The processor receives the Tag ID and Object ID from the at least one originating device, and uses at least the received Tag ID and Object ID to look up a corresponding action in the action table. A servicing node in the system receives the action and performs at least partial execution of the action, thereby generating results comprising the customized service.

The invention also comprises a method for providing a customized service in a network. (See FIG. 1a) The method comprises the steps of generating an identifier of one of a user and a product associated with the user (Tag ID) and an identifier of the service (Object ID). The Tag ID and Object ID are transmitted to a separate processing node. An action is determined at the processing node based on at least the received Tag ID and Object ID. The determined action is executed and results based on the determined action are generated, the generated results comprising the customized service.

The invention further comprises a look-up and routing service for providing a customized service to an end user via a network. The service includes receiving an identifier of one of a user and a product associated with the user (Tag ID) and an identifier of the service (Object ID). The Tag ID and Object ID are processed and an action corresponding to the received Tag ID and Object ID is determined. Execution of the action and generation of results based on the determined action is initiated, the generated results comprising the customized service.

DETAILED DESCRIPTION

Figure 1:
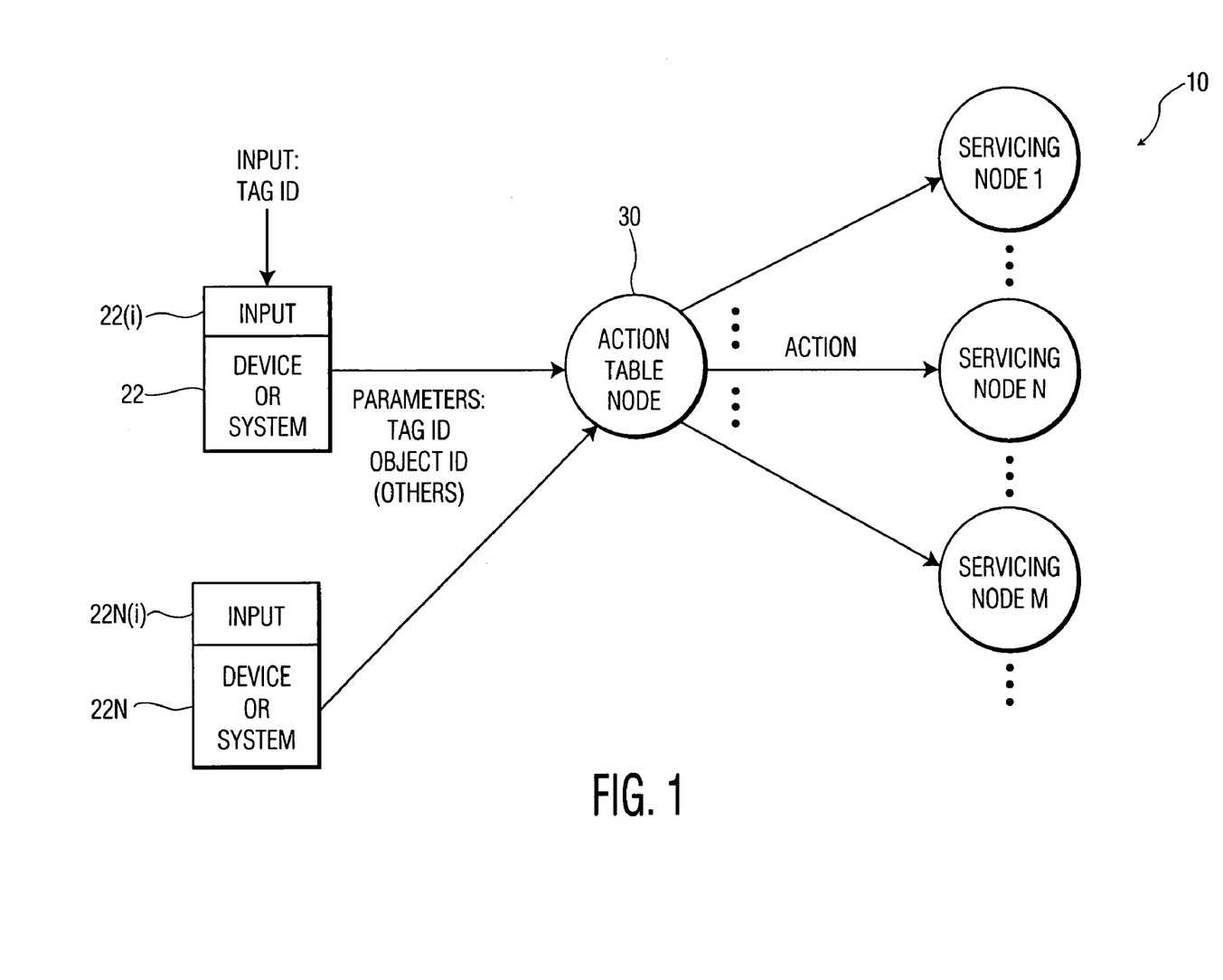
FIG. 1 is a first embodiment of the network of the present invention.
Figure 1A:
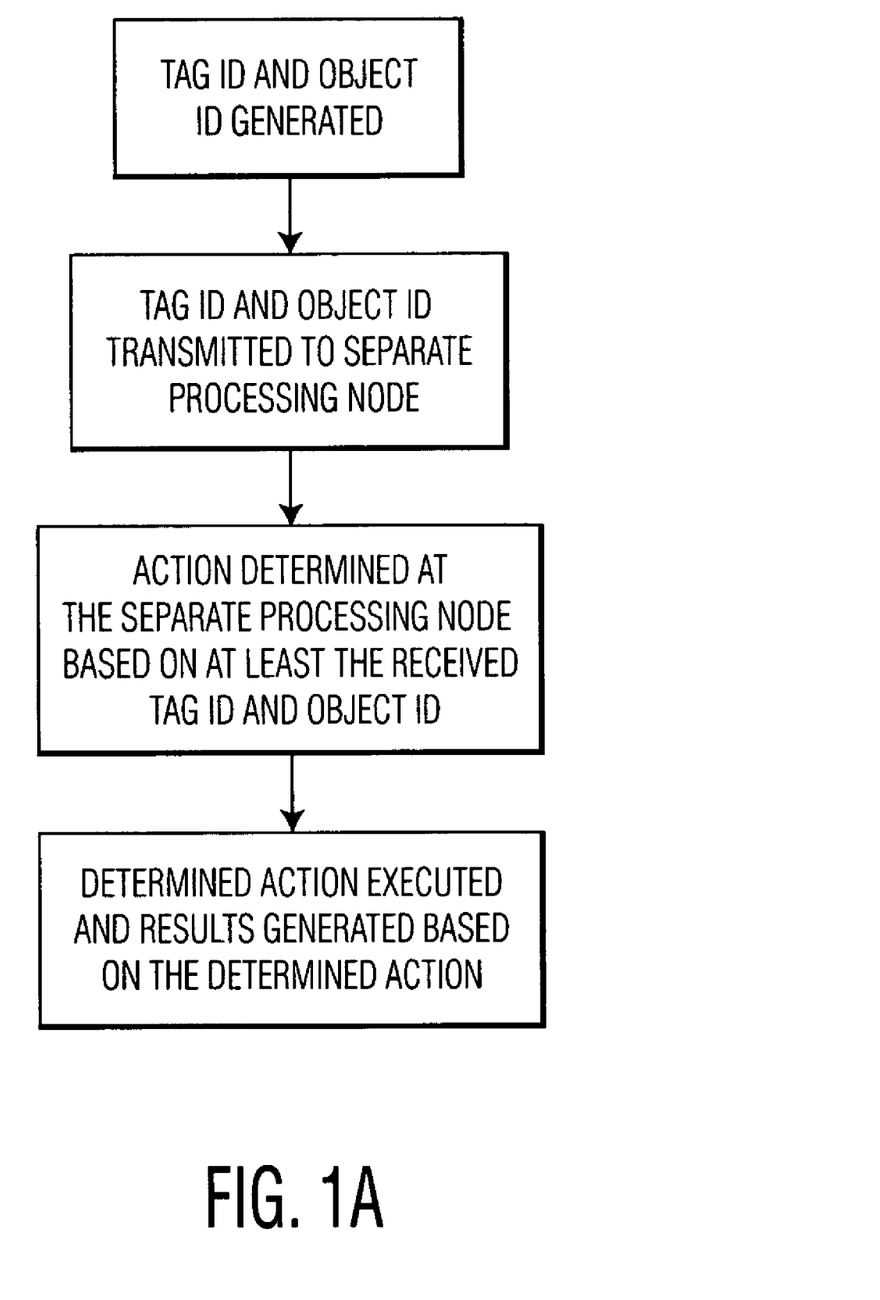
FIG. 1a is an embodiment of a method included in the present invention.

Referring to FIG. 1, a network 10 embodying the present invention is shown. At the user's end, device or system 22 is shown as a user node of the network and in general represents the entry point to the network at the user end. The device or system 22, or, as described further below, a service to be invoked via the device or system 22 is identified by an "Object ID". Another identifying parameter is generated at the user end, namely a "Tag ID" which identifies a user, a user surrogate, or an object that utilizes device or system 22 or otherwise invokes the service identified by Object ID. The Tag ID may be input by an input 22(i) associated with device or system 22, or it may be generated internally by device or system 22. The Tag ID and Object ID are parameters that are transmitted from device or system 22 into the network. Additional parameters, labeled "others" in FIG. 1, may also be transmitted into the network. As described further below, other parameters may include, for example, pertinent sensor data at or near the input 22(i).

When needed, input 22(i), which may be a reader, sensor, touchpad, keyboard, etc., provides an input for a Tag ID at the associated device or system 22. For example, input 22(i) may be a bar code scanner that reads a bar code (Tag ID) on the label of a shirt. As another example, input 22(i) may be a magnetic sensor that reads the magnetic strip of an employee identification (Tag ID). As another example, input 22(i) may be an RF identification reader that reads an employee identification comprised of an RF tag (Tag ID). Such an RF tag may, for example, comprise a transponder that stores ID data in a non-volatile memory and transmits the ID data by modulating an RF resonant frequency generated by the RF identification reader. There may be components associated with such readers that provide further processing and/or formatting of the Tag ID. For example, if input 22(i) is a magnetic sensor, then there may be an A/D converter and a microprocessor that receives the magnetic data and reformats the Tag ID into a form that is compatible with the network. Although one device or system 22 is focused on in FIG. 1, it is understood that there may be many (as represented by device/system 22N and optional input 22N(i)) that perform essentially the same functions receiving and/or generating and transmitting a Tag ID, Object ID and other parameters (if any) into the network 10. The various devices or systems 22 may be alike and/or different.

The Tag ID, Object ID and any other parameters from reader 20 are transmitted into the network 10 to an action table node 30. The action table node 30 may be a server on which an action table resides. The action table includes various actions, each of which are a function of one or more parameters. Thus, for the particular Tag ID, Object ID and any other parameters received by the server from reader 20, the server uses the parameters as indices for looking up a corresponding action in the action table.

The action retrieved from the action table corresponding to the Tag ID, Object ID and any other parameters received from reader 20 will generally also designate a servicing node for servicing the action. Referring to FIG. 1, multiple servicing nodes 1, . . . , N, . . . , M are shown linked in the network 10 with action table node 30. FIG. 1 shows that servicing node N is designated to perform the action retrieved from the action table. Accordingly, appropriately formatted control commands comprising the action are transmitted from the server of the action table node 30 to servicing node N, also for example comprised of a server (or servers). Once received by servicing node N, the action is executed and corresponding results are generated, initiated, processed and/or output by the servicing node N.

EXAMPLE 1

Figure 2:
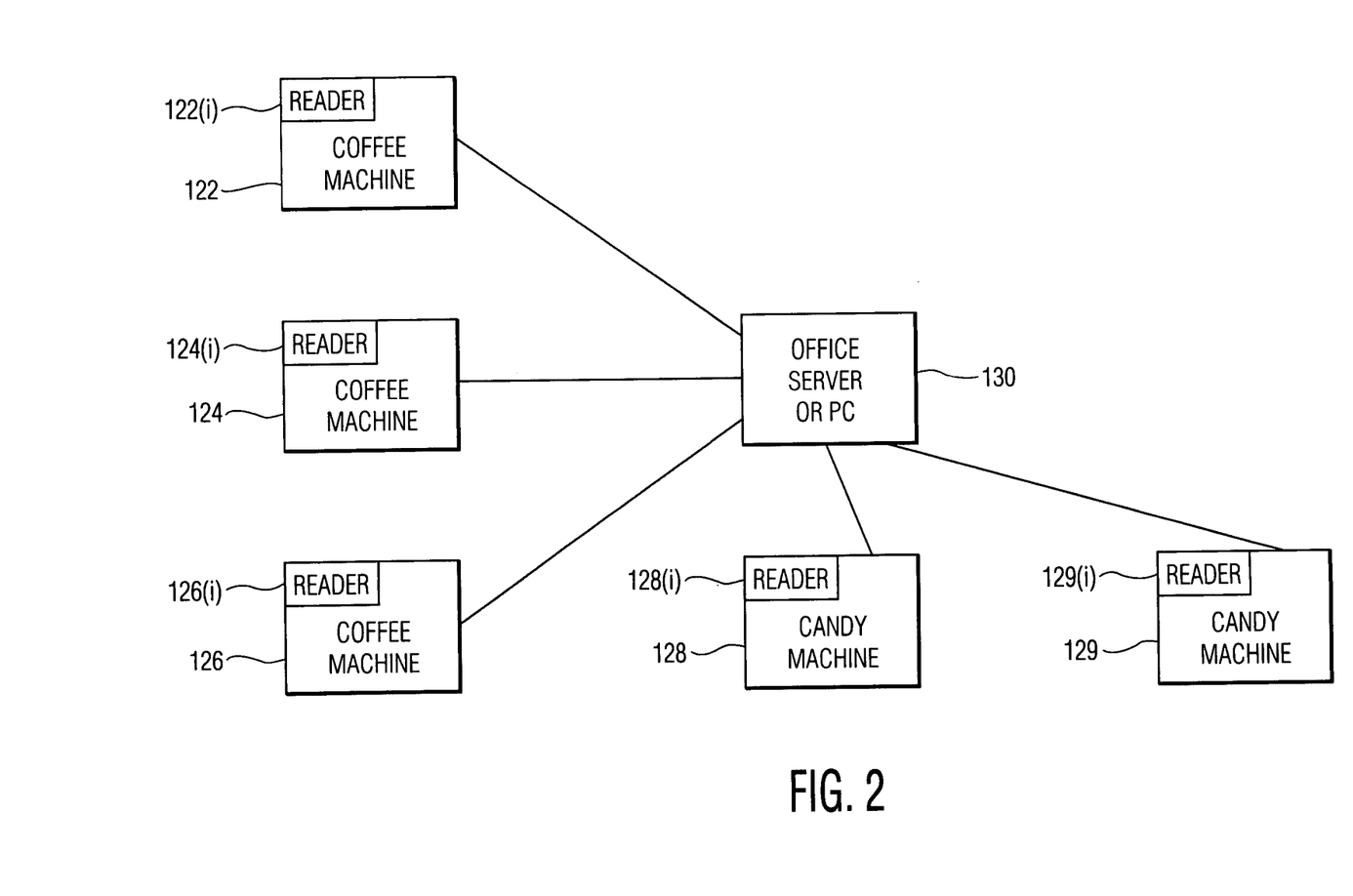
FIG. 2 is an exemplary embodiment of a network of the present invention.

FIG. 2 shows the invention implemented in a local work environment, such as a large plant complex. Office server 130, which may be a PC, supports the action table and also provides the service or results. Three coffee machines 122-126 having three respective attached readers 122(i)-126(i) are located throughout the complex. Each coffee machine 122-126 interfaces with office server 130, for example by wire or wireless connections. Readers 122(i)-126(i) are, for example, RF identification readers that read an RF tag on the identification cards of plant employees, or magnetic card readers that read the magnetic strips on the identification cards of plant employees, which gives the employee identification number. The employee identification number is the Tag ID.

Readers 122(i)-126(i) may be integral to coffee machines 122-126, or attached to or otherwise associated with coffee machines 122-126. The electronics associated with processing at the coffee machine may reside in the coffee machine, its reader, or both. For convenience, each coffee machine 122-126 and its respective reader 122(i)-126(i) will be considered one comprehensive device in the description.

Action table on server 130 stores a preference for each employee that reflects the employee's coffee brewing preference at the coffee machines 122-126. The preference is retrievable from the action table using the employee's identification number (Tag ID) and an Object ID of the coffee machine 122-126. Thus, when employee A swipes his or her identification card at reader 124(i) of coffee machine 124, for example, the internal electronics of the coffee machine 124 reads the employee identification number and transmits it to server 130, along with the Object ID for coffee machine 124. (Alternatively, an Object ID for coffee machine may be recognized internally by server 130 where coffee machine is separately wired to server 130.) Server 130 uses the Object ID and Tag ID to consult action table on server 130 and retrieve employee A's coffee preference (for example, decaf, with milk and sugar). A signal is returned to the coffee machine 124 indicating how the coffee should be brewed. The internal processing electronics processes the received command and coffee machine 124 outputs the preferred coffee for employee A.

The coffee preference (action) may be a function of additional parameters, such as time of day, date, temperature, etc. These parameters may be received at the server 130 from external sensors, an internal clock and calendar, etc. For example, if it is summer, the corresponding preference for employee A may be ice coffee. Thus, there may be multiple entries in the action table for an employee.

Certain additional signal processing steps may be involved in the signal generation and processing. For example, the internal processing electronics of coffee machines 122-126 may include an A/D converter that converts the RF, magnetic, optical, or other codes on the employee identification cards into a digital signal that is transmitted to server 130. Alternatively, server 130 may perform the A/D conversion. Additional signal processing may be required to transform the employee identification number into a format that may be used by the server to access the corresponding preference in the action table. The signal that server 130 returns to the coffee machine that reflects employee A's preference may also be reformatted in order to properly control the mixing hardware of the coffee machine.

Server 130 routes the control signals to the coffee machine where the employee swiped his or her ID card. Although they are each coffee machines, it is preferable that each coffee machine 122-126 have a unique Object ID, so that server 130 may identify the particular coffee machine submitting the parameters, properly format the control signal result for the particular coffee machine, and route the control signal result to the proper coffee machine. This may require that a separate coffee preference entry be made for each employee Tag ID and each coffee machine Object ID in the action table. Alternatively, a single action table entry for an employee's coffee preference may be accessed using the employee's Tag ID and any one of the Object IDs for the coffee machines 122-126.

At least a portion of the servicing node resides with the action table node on the office server 130 in the example of FIG. 2. That is, the execution of the action retrieved from the action table and the generation of a result, namely the control signal for the coffee machine based on the employee's coffee preference retrieved from the action table, is generated and output by server 130. Another portion of the result, namely the proper brewing of the coffee, is carried out by the coffee machine.

In a large plant complex, a large number of employees may converge on a limited number of coffee machines at certain times, for example, a 15 minute morning coffee break. If each employee in line must manually input his or her coffee selection, then only a limited number of employees will be able to have coffee (resulting in employee discontentment) or else the coffee break will unofficially be extended (resulting in plant inefficiencies). Thus, the network of this embodiment enables the coffee machines to be used at their maximum capacity to accommodate the largest number of employees.

The network and action table may control other devices or systems in the plant complex or be expanded to include them as new devices or systems are added. For example, also shown in FIG. 2 are candy machines 128, 129, along with their associated readers 128(i), 129(i). Action table 130 also includes data that associates a preferred candy selection with the employee ID (Tag ID) of each employee and the Object ID of each candy machine. The action table 130 thus has entries associated with employees' coffee preferences (referenced by the employee's Tag ID and Object ID of the coffee machines) and entries associated with employees' candy machine preferences (referenced by the employee's Tag ID and the Object ID associated with the candy machine).

The software associated with the action table 130 determines which entry of the action table to consult based upon the parameters received. When an employee, such as employee A, swipes his or her ID card at reader 128(i) of candy machine 128, the server 130 receives employee A's employee identification number (Tag ID) and Object ID for candy machine 128. Server 130 uses the two parameters (Tag ID and Object ID) to consult the action table. A candy preference for employee A is retrieved from the action table and a corresponding command signal is returned from the server 130 to candy machine 128 instructing the preferred candy to be dispensed.

The network and action table 130 of the plant facility may be further expanded to include other devices and systems. For example, the settings at work stations may be automatically re-adjusted when a new shift arrives and employees swipe their ID cards at readers associated with a respective work station. The employee ID (Tag ID) and work station identifier (Object ID) is sent to the server 130, where settings for the employee pertinent to the work station are retrieved and returned to the work station for automatic re-adjustment of the settings.

EXAMPLE 2

Figure 3:
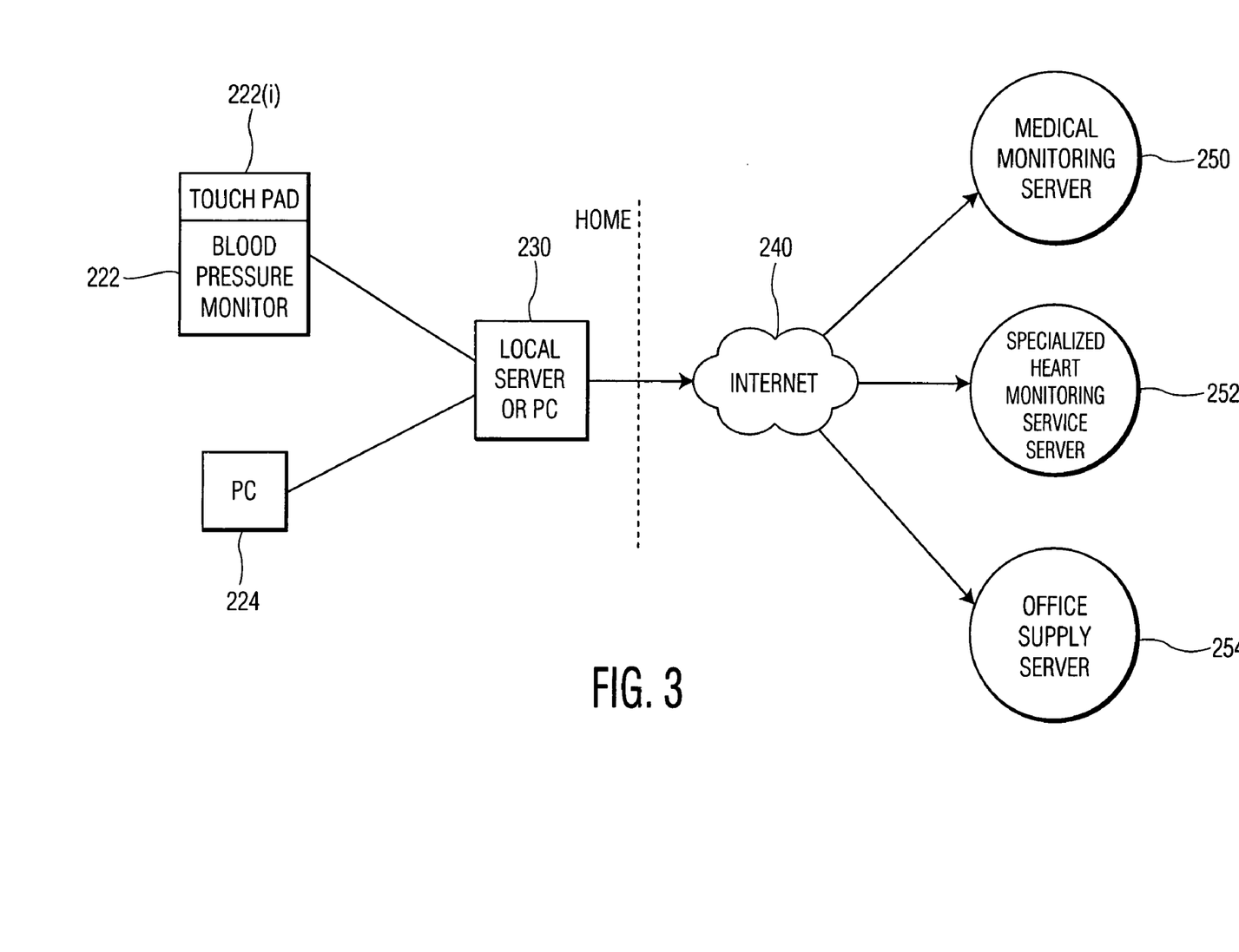
FIG. 3 is another exemplary embodiment of a network of the present invention.

FIG. 3 shows the invention implemented in an Internet network context. In this example, the action table is stored on a server or PC 230 in a local environment, in this case a home. A device in the home, for example, a blood pressure monitor 222 has an associated input 222(i), such as a touchpad. Person A inputs an ID code (Tag ID) at touchpad 222(i) and then straps on the blood pressure monitor 222, which captures a reading of the his or her blood pressure. Parameters comprised of the Tag ID, a blood pressure monitor identifier (Object ID) and the blood pressure reading are transmitted by internal processing electronics of the blood pressure monitor 222 to server 230. Server 230 uses the Tag ID and Object ID parameters to retrieve a corresponding action from the action table, for example, a web address for the server 250 of a medical monitoring service used by person A's doctor, as well as a direction to transmit the blood pressure reading and Tag ID of person A to medical monitoring server 250 for processing.

Server 230 uses the retrieved web address to link with the server 250 of the medical monitoring service over the Internet 240. Person A's identity and blood pressure reading are transmitted from home server 230 to the server 250 of the medical monitoring service, along with the instructions (action) for processing. Generally, the processing conducted by the medical monitoring service server may include compiling blood pressure readings for person A, along with the date and time of the reading. The compiled readings may then be retrieved and analyzed from server 250 by person A's doctor.

If, however, an abnormal reading (unusually high, for example) is received by medical monitoring service, a corresponding supplementary instruction (action) may be retrieved from a memory associated with server 250. The supplementary instruction may comprise routing person A's identity, web address and blood pressure reading to a specialized heart monitoring service server 252, as well as instructions for additional processing by the specialized heart monitoring service server 252. The supplementary instruction may also include retrieving additional pertinent information regarding person A pre-stored in the memory of server 250 (such as person A's age, sex, weight, normal blood pressure, physician, etc.) and transmitting the additional information to the specialized heart monitoring service server 252, along with person A's identity, web address and blood pressure reading.

When the information is received, the processing conducted by the specialized monitoring service server 252 may be an extended analysis of the blood pressure that takes into account the additional pertinent information received regarding person A. A summary of the findings of the extended analysis are returned to the web address of the blood pressure monitor 222 and displayed, for example, on an LCD display thereon (not shown in FIG. 3). If the extended analysis indicates a dangerous blood pressure level, for example, an alert may be returned instructing person A to seek immediate medical attention. Server 252 may also look up the phone number of person A's physician in a memory associated with server 252 and initiate an appropriate telephone alert to the physician's office regarding person A's condition.

Thus, the action transmitted by server 230 may result in a pipeline or chaining of successive services by successive servers. In addition, the action table in the above example may be considered as distributed between a number of network nodes, namely local server 230 and medical monitoring service server 250. Thus the local server 230 houses what may be considered a "primary" action table which included the web address for the server 250 of the medical monitoring service, as well as the direction to transmit the blood pressure reading and Tag ID of person A to medical monitoring server 250 for processing. In the case of medical monitoring server 250, what may be considered a "secondary action table" in the associated memory included supplementary instructions for routing person A's identity, web address, blood pressure reading and other pertinent information to a specialized heart monitoring service server 252 for processing when abnormal blood pressure conditions are detected.

Alternatively, the blood pressure reading parameter (along with the Tag ID and Object ID parameters) may be used by action table server 230 to look up a corresponding action on the action table. If the blood pressure reading is in a normal range, then the retrieved action will be instructions to send the blood pressure reading parameter and the Tag ID to the medical monitoring service server 250 to be added to the compilation of A's prior readings, as described above. If the blood pressure reading is excessively high, then the retrieved action by action table server 230 may instruct that the pressure reading and other pertinent information be sent directly to the specialized heart monitoring service server 252, along with an instruction for processing, in the manner described above. For extremely high readings, where further analysis is unnecessary, the retrieved action from the action table of the local server 230 may be to invoke the services of a local ambulance corp. Thus, the action retrieved from the action table may invoke multiple services or results, depending on the parameters received.

By separating the servicing of actions to servicing nodes connected to the Internet, this exemplary embodiment vastly expands the numbers and types of results that can be directed via actions retrieved from the action table. Instead of limiting the results to those that may be achieved locally by a local device, system or software processing, as in Example 1, actions that may be stored in the action table, and corresponding results that may be achieved when those actions are invoked by parameters, are any that may be provided by or through accessible servers connected to the Internet.

EXAMPLE 3

The system of FIG. 3 may also be expanded to include other readers for other devices or systems in the home or other local environment. With the addition of other devices and/or systems, the action table on server 230 is commensurately expanded to include actions corresponding to Tag IDs, Object IDs and any other parameters received from the other devices and/or external sensors.

In addition, the action table of the invention may accommodate parameters that are different or more abstract than the Tag ID directly associated with a person's identity or an Object ID associated with a local device or system in the examples given above. For example, in FIG. 3, PC 224 comprises another entrance node by the user into the network supporting the invention. The PC has an internal identifier that is transmitted with other parameters into the network, thus comprising a Tag ID. (The Tag ID of the PC may be viewed as the user's or household's Tag ID, but it is different from the above-described scenarios because it generally does not require manual input of a Tag ID by a user of the PC.)

In one particular example, PC desktop has a "Paper" icon that a member of the household clicks when he or she wants to re-order a standard quantity of paper for a home office, for example. By clicking the paper icon, PC 224 transmits to server 230 the Tag ID and a parameter associated with a paper order. Object IDs of prior examples were directly associated with a local device, such as a vending machine or a blood pressure monitor (and thus may be considered a "device ID", or, alternatively, an "input ID" or "reader ID"). However, it is also noted that the Object ID in these prior examples may also be considered as identifying a service desired by the user that happens to be provided by the local devices in the prior examples. In this case, the paper order parameter is associated with a remotely provided service desired by the person or household associated with the PC. Thus, the paper parameter is categorized as an Object ID (which may alternatively be viewed as a "service ID"). Server 230 uses the Tag ID and Object ID parameters to retrieve a corresponding action from the action table. The action retrieved may be, for example, instructions for ordering over a particular office supply website a particular amount and type of paper for delivery, which correspond to the home office's standard paper order. The order is formatted by server 230 and sent to the office supply server 254 via the Internet 240.

EXAMPLE 4

Figure 4:
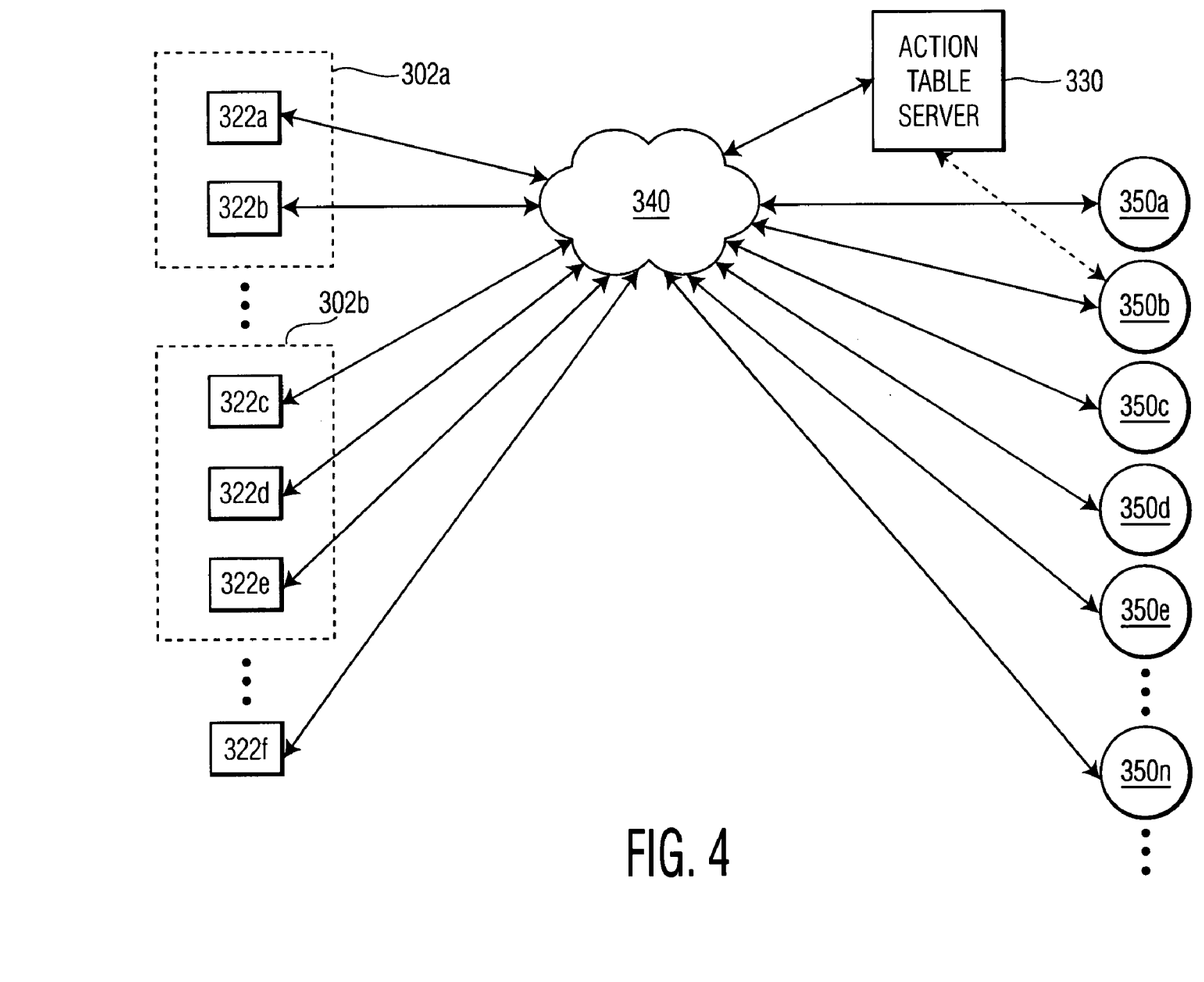
FIG. 4 is yet another exemplary embodiment of a network of the present invention.

FIG. 4 shows another exemplary embodiment of the invention implemented in an Internet network context. In this example, the action table is stored on a separate server 330 integrated into the Internet. To the left of the dashed line are a multiplicity of devices 322*a-f* that interface with the Internet and submit parameters such as Tag IDs and Object IDs in accordance with the invention. The devices may be grouped together in localities, such as a home, office, amusement park, college, plant, etc., as represented by devices 322*a*, 322*b* shown in group 302*a* and devices 322*c*, 322*d*, 322*e* shown in group 302*b*. Other devices may be mobile and not necessarily restricted to a locality, such as a laptop PC, PDA, cellphone, etc., which are represented by device 322*f*.

As shown, action table resides on a server 330 that forms a separate node in the Internet 330. Also shown are additional nodes 350*a*, 350*b*, 350*c*, . . . , 350*n*, . . . of the Internet, which are servicing nodes of the invention. The additional nodes 350*a*, 350*b*, 350*c*, . . . , 350*n*, . . . may in theory be any server attached to the Internet that may generate a result or otherwise perform a function. Thus, there are potentially a large number of servicing nodes that interact with action table server 330 in accordance with the invention, as represented by servicing server 350*n* in FIG. 4.

As in the above embodiments, parameters are generated at a device and transmitted to the action table. For example, a Tag ID, Object ID and other optional parameters may be generated by user initiation at device 322*a*. Device 322*a* links with action table server 330 through the Internet 340, and transmits the parameters to server 330. The processing then proceeds analogously to the previously described embodiments, namely, the submitted parameters Tag ID, Object ID and any others are used to look up a corresponding action in the action table. Server 330 initiates the retrieved action. For example, based on the retrieved action, action table server 330 may link with servicing server 350*b* via the Internet 340 (as represented by the dashed line between action table server 330 and servicing server 350*b*), submit commands based on the retrieved action to server 350*b*, which executes the action and generates results corresponding to the action.

The generated results may be transmitted from servicing server 350*b* back to device 322*a* through the Internet 340. Alternatively, the results of servicing server 350*b* may invoke the services of other servicing servers or a service outside of the Internet, generating further results corresponding to the retrieved action. Alternatively, the server 330 supporting the action table may transmit a result directly back to device 322*a* through the Internet. In general, the examples of prior embodiments may be readily adapted to the inclusion of the action table in separate server 330 connected to the Internet 340. As will be discussed further below, this embodiment provides for economies of scale and an action table service that may be expanded to an indefinite number of users, devices and services. A number of specific examples of this embodiment are now given.

In a variation of the embodiment that included vending machines at a plant given in Example 1 above, the coffee machine manufacturer may offer a service to its customers, in this case, the owner of the plant facility. In FIG. 4, coffee machines may be considered devices 322*c-e* in locality 302*b*, namely, the plant. Coffee machines 322*c-e* each have employee ID card readers as described above (but not separately shown in FIG. 4), thus enabling each employee to submit a Tag ID when getting coffee at the machine. Each coffee machine also stores an Object ID identifying the coffee machine. When the Tag ID for employee A is read at the coffee machine 322*c*, for example, an internal microprocessor connected with the Internet 340 links with action table server 330 and transmits the Tag ID and Object ID for coffee machine 322*c* to action table server 330.

In one case, the coffee machine manufacturer may itself maintain the action table server 330. A list of Tag IDs for employees and their corresponding coffee preferences are submitted to the manufacturer and periodically updated. The manufacturer uses this data to create coffee preference entries on the action table, each preference referenced by a Tag ID and the Object ID of each of the coffee machines 322*c*, 322*d*, 322*e* at plant 302*b*. Thus, when the Tag ID for employee A and Object ID for coffee machine 322*c* are submitted to action table server 330 over the Internet 340, the coffee preference of employee A is retrieved from the action table. In this case, action table server 330 formats a command for coffee machine 322*c* corresponding to employee A's coffee preference and returns the command via the Internet 340 to the originating Internet address of coffee machine 322*c*. Coffee machine 322*c* receives the command and dispenses coffee according to employee A's preference. The coffee machine manufacturer may provide similar services to other offices, plants, etc. For example, locality 302*a* in FIG. 4 may be an office having two coffee machines 322*a*, 322*b* that likewise access the action table server 330 of coffee machine maker via the Internet 340.

In another variation, the action table server 330 is a separate service provider. That is, it is not maintained by the coffee machine manufacturer, but instead provides a service to the manufacturer and/or the plant owner for a fee. In that situation, the action table may provide action look-up services for many types of end services or actions for many separate clients and/or customers. Thus, it may not be desirable for the action table server 330 itself to consume resources by processing and returning dispensing commands directly to coffee machine 322*c* based on the retrieved preference. Accordingly, server 330 may act principally as a router in that the action retrieved from the action table by server 330 may comprise a simple command that is routed to and executed by another servicing server, thereby invoking a service and fulfilling a user's need.

For example, the action retrieved from action table corresponding to employee A's Tag ID and coffee machine's 322c Object ID may be a customized web address on the coffee machine manufacturer's website (e.g., servicing server 350a) that includes data for employee A. In particular, the customized web address may include command controls for coffee machine 322c that correspond to employee A's coffee preference. In addition, where the Object ID is an identifier that uniquely identifies the particular originating coffee machine 322c, then the Object ID is more in the nature of a particular device identifier (or, alternatively, an identifier of a service provided by a particular device). In that case, the customized web address retrieved from the action table is customized for employee A's preferences at the particular originating coffee machine 322c. Thus, the customized web address on servicing server 350a may also include the originating web address of coffee machine 322c.

After the customized web address corresponding to employee A's Tag ID and coffee machine's 322c Object ID is retrieved from action table, action table server 330 processes the address and links with employee A's customized web address on server 350a. At the servicing server 350a, the invocation of the customized web address initiates processing that results in the coffee service being provided to employee A at coffee machine 322c. Thus, servicing server 350a links with the web address of the coffee machine 322c, as found in the customized web address. Control commands for employee A's preferences, as also found in the customized web address, are transmitted by server 350a to coffee machine 322c. Coffee is thus dispensed at coffee machine 322c according to employee A's preference.

In the example described immediately above, the Object ID uniquely identified the originating device. Thus, the web address of the originating device was correlated to the Object ID in the action table or in the servicing node. In a variation of the embodiment described immediately above, the Object ID does not uniquely identify the particular originating device. Instead, the Object ID may be an identifier of a class of devices or systems, or, alternatively, a service provided by a class of devices or systems. In that case, the web address of the particular originating device may need to be transmitted to the servicing server, so that results may be returned to the particular originating device. Because the action table is part of a separate Internet node (330) in FIG. 4, when a device 322a-322f links with the action table server 330 to transmit parameters, action table server 330 automatically receives the Internet address of the particular originating device 322a-322f. Thus, action table server 330 inherently knows the web address of the originating device, and may thus also transmit the originating web address of the particular originating device to the servicing node (along with the action retrieved from action table). This allows the servicing node to return results to the originating device via the Internet.

For example, in the above coffee machine example, if coffee machines 322c-e are identical makes and models, then they each respond to the same dispensing commands and may thus all have the same Object ID. One action is stored in action table on action table server 330 corresponding to employee A (Tag ID) and the Object ID applicable to all three coffee machines. The action stored for the Tag ID and Object ID (applicable to all three identical coffee machines 322c-e) may be a customized web address on the coffee manufacturer's server 350a. The web address on the coffee maker manufacturer's server 350a is customized for employee A's preferences at the class of coffee machines identified by the Object ID, such as coffee machines 322c-e.

When employee A swipes his or her ID card at a particular coffee machine (e.g., coffee machine 322c), action table server 330 receives the Tag ID of employee A and the Object ID corresponding to the class of coffee machines. In addition, action table server 330 knows the web address of the particular originating device 322c via existing Internet protocols. Using the Tag ID and Object ID, action table server 330 invokes the customized web address on coffee maker manufacturer's server 350a, as retrieved from the action table, and also transmits the web address of the particular originating coffee machine 322c to coffee maker manufacturer's server 350a. As noted, at the coffee maker manufacturer's server 350a, invocation of the custom web address initiates processing that results in the coffee service being provided to employee A. Control commands for employee A's preferences at the class of coffee machines corresponding to the Object ID, including originating coffee machine 322c, are found in the customized web address. Coffee maker manufacturer's server 350a sends the control commands back to particular coffee machine 322c using the web address for coffee machine 322c received from action table server 330.

The examples provided above also indicate that the service need not necessarily be provided at the device at which the person invokes the service. For example, in the coffee vending machine examples, the employee may initiate the service in one part of the office, while the coffee is dispensed at a coffee machine in another part of the office. For example, employee A may have a "coffee" icon on the desktop of the PC in his or her office. When the icon is clicked, coffee is dispensed at the closest coffee vending machine in the office, such as coffee machine 322c. Thus, employee A may click the icon and then walk down the hall to coffee machine 322c, where his or her cup of coffee will be waiting.

Specifically, PC has employee A's Tag ID and the Object ID for coffee machine 322c pre-stored in memory. When the desktop "coffee" icon is clicked, the PC transmits to action table server 330 employee A's Tag ID, the Object ID and, if necessary, the web address for particular coffee machine 322c. The processing by the action table server 330 and coffee maker manufacturer's server 350a proceeds in one of the manners described above, resulting in coffee being dispensed according to employee A's preference at coffee machine 322c.

As noted above, action table server 330 may be a commercial service that principally stores actions in action table applicable to a multiplicity of different devices, systems or services (as identified by an Object ID) for a particular person (Tag ID). The various services supported by the action table server 330 may be distinct from one another and paid for separately. The action table may also be expanded to incorporate new services, by entering new actions referenced by Tag ID, Object ID and any other pertinent parameters.

For example, another service that action table server 330 may provide in addition to the automatic coffee dispensing service is a clothes alert service for washing machines. Thus, the action table further includes action entries corresponding to the Tag IDs pertinent to the on-line clothing alert service and the Object IDs pertinent to the service, described further below, in addition to the coffee preference entries described above, referenced by the Tag ID of persons receiving the coffee preference service and the Object ID of the coffee machines used in providing that service.

In the example of the clothes alert service, device 322b is a washing machine in home 302a. Washing machine includes, for example, a magnetic reader that reads a magnetic strip in clothing being put into the washing machine. The magnetic strip may be embedded in an article of clothing by a manufacturer and coded with an identifier of the manufacturer and article of clothing, described further below. A memory associated with a microprocessor in the washing machine 322b stores any clothing identifiers, which comprise Tag IDs. For ease of description, one such clothing identifier, representative of a blue Gap cotton tee shirt, is presumed to be read and stored below. Once all the clothes are entered, the user enters the desired settings on the machine (such as "hot water wash, cold rinse, regular cycle") and presses start.

Because a clothing identifier is stored in the washer's 322b memory when start is pressed, the washing machine does not immediately start, but first invokes the clothes alert service. The microprocessor of the washing machine 322b is connected to the Internet 340 and links with the action table server 330. The washing machine 322b transmits a number of parameters to the action table server 330, namely the clothing identifier (a Tag ID) and a washing machine device identifier (an Object ID), and the washing machine settings (additional parameters). Action table server 330 uses the received Tag ID and Object ID to retrieve a corresponding action from action table related to washing instructions for the blue Gap cotton tee shirt.

The action may include, for example, a customized web address on the Gap server (for example, server 350c) relating to washing instructions for the blue cotton tee. The retrieved action may instruct the action table server 330 to link with the customized Gap web address on server 350c and transmit the washing machine settings thereto, along with the originating address of the washing machine 322b. By linking with the customized Gap web address and transmitting the washing machine settings as input, the Gap server is invoked to evaluate the propriety of the washing machine settings in view of the Gap washing instructions for its blue cotton tee. If the washing machine settings are inappropriate for the shirt, the Gap server 350c returns a result to washing machine 322b in the form of an alert. If the setting is appropriate, a proceed signal is sent to the washing machine 322b, so that washing machine 322b may initiate its wash cycle. As noted, Gap server 350c is able to return the result directly to washing machine 322b because action table server 330 transmits the web address of washing machine 322b with the other washing machine setting parameters to Gap server 350c.

Once again, it is seen that the action table server 330 of this embodiment acts principally as a look-up table and router of action commands to servicing servers 350a, 350b, 350c, . . . , 350n, . . . on the Internet. By separating the execution of actions retrieved from the action table server and placing the execution of the retrieved actions in separate servicing servers on the Internet, the action table server can accommodate more hits, because the processing is limited to retrieval of a corresponding command and routing to a servicing server. In addition, the number and types of activities that may be serviced can expand dramatically, theoretically including any server that is connected to the Internet and which provides a service or result. Because the action table includes a uniform format (that is actions are referenced by Tag ID, Object ID and possibly other parameters), the action table can be readily expanded to include new entries for existing services, as well as new entries for new services. Thus, for example, all of the specific examples given herein with respect to FIG. 4 and many others, may be supported by the action table of action table server 330. In addition, if the number of activities and hits grows, additional action table servers may be introduced to increase processing speed, with each action table accessing a comprehensive database on which the action table is stored. Alternatively, each action table server may have a separate database on which entries for a group of services are stored.

As one final example of the versatility of the present embodiment, a variation of the prior paper ordering example is used. In this case, device 322f is a cell phone that includes processing and display functions (for example, PDA functions). The cell phone 322f includes a Domino's pizza icon that the user selects when he or she wants to place a standard order at the closest Domino's pizzeria. By selecting the icon, the cell phone processor transmits a cell phone identification number (Tag ID) and a Domino's pizza identifier (Object ID) to the action table server 330 via the Internet 340. It is noted that in this example, the cell phone transmission must access the Internet via a wireless gateway.

The action table server 330 receives the cell phone identification number (Tag ID) and Domino's pizza identifier (Object ID) parameters from the cell phone 332f and uses them to retrieve corresponding action commands from the action table. A first component of the action retrieved from the action table, for example, includes a particular web address at the cell service provider's server (such as server 350d) that is customized for the cell phone 322f with the Tag ID. The action table server 330 links with the customized web address and, by doing so, the processing invoked at the cell service provider server 350d includes (1) determination of the approximate location of the cell phone 322f, which is known by the base station servicing the cell phone 322f and (2) transmission of the approximate location of the cell phone 322f from the cell service provider server 350d to the action table server 330.

After action table server 330 receives the location of cell phone 332f, a second component of the action retrieved from the action table is initiated. The second component of the action retrieved from action table also includes a particular web address at the Domino's server (such as server 350e) that corresponds to the cell phone 322f with the Tag ID. The particular web address in the Domino's server 350e includes the cell phone owner's standard order. Action table server 330 links with the particular web address on the Domino's server 350e and transmits the cell phone location to the Domino's server 350e. By linking with the Domino's web address, processing invoked in the Domino's server 350e includes determining the closest Domino's pizzeria to the cell phone location and submission of the standard order to the determined closest Domino's pizzeria, along with the cell phone number. The receiving Domino's pizzeria makes the appropriate pizza and calls the cell phone to find out the address to deliver the pizza.

Thus, this example again shows the action retrieved from the action table as being executed by a succession of servers (which run back through the action table server node) before the final results are achieved. In this case, the simple pressing of an icon on a user's cell phone automatically results in delivery of a standard service (a pizza order) from a service center (a Domino's pizzeria) in closest proximity to the user.

The compiling and pre-storing of entries (commands) in the action table corresponding to a Tag ID, Object ID and any other parameters in the above examples may be done in any of a myriad of standard methods and programming techniques well known in the art. The particular method or technique selected for building the action table will likely correspond to the role the action table server plays, for example whether it is on a local server dedicated to one or a few services in a plant or other local environment, or a separate servicing and routing node provided by a separate commercial entity for many different end services and users. In the latter case, the action table server may provide an Internet "account" through which users may access and adjust their action table entries to change their preferences.

Although illustrative embodiments of the present invention have been described herein with reference to the accompanying drawings, it is to be understood that the invention is not limited to those precise embodiments, but rather it is intended that the scope of the invention is as defined by the scope of the appended claims.

What is claimed is:

1. A system for providing a customized service in a network, comprising:
at least one originating device that provides an identifier of one of a user and a product associated with the user (Tag ID) and an identifier of the customized service (Object ID); a processor having an associated action table, the processor receiving the Tag ID and Object ID from the at least one originating device, the processor using at least the received Tag ID and Object ID to look up a corresponding action in the action table; and a servicing node that receives the action and performs at least partial execution of the action to provide a customized output corresponding to at least the Tag ID and Object ID.

2. The system as in claim 1, wherein the at least one originating device has an associated input that receives the Tag ID as input.

3. The system as in claim 1, wherein the servicing node that receives the action and performs at least partial execution of the action corresponds to the at least one originating device, the originating device generating results comprising the customized service.

4. The system as in claim 3, wherein a single server comprises the processor and the servicing node.

5. The system as in claim 1, wherein at least a part of the customized service identified by the Object ID is provided by the originating device.

6. The system as in claim 5, wherein the performing of at least partial execution of the action by the servicing node to generate results includes generating control commands based on the received action and transmitting the control commands to the originating device, the control commands provided to the originating device corresponding to the customized service provided.

7. The system as in claim 1, wherein the processor receives at least one parameter in addition to the Tag ID and Object ID, the processor using the received at least one parameter along with the Tag ID and Object ID to look up a corresponding action in the action table.

8. The system as in claim 1, wherein the servicing node that receives the action and performs at least partial execution of the action comprises a servicing server at a network node separate from a network node that includes the processor and the associated action table.

9. The system as in claim 1, wherein at least a part of the customized service identified by the Object ID is provided by an external service provider.

10. The system as in claim 9, wherein the performing of at least partial execution of the action by the servicing node to generate results includes generating instructions based on the received action and transmitting the instructions to the external service provider, the instructions corresponding to the customized service provided by the external service provider.

11. The system as in claim 1, wherein the system provides multiple customized services, each identified by an Object ID, each such customized service provided to multiple Tag IDs, the action table having at least one action corresponding to each combination of Object ID and Tag ID for each such customized service.

12. The system as in claim 11, wherein the system comprises multiple servicing nodes, a particular action looked up in the action table determining the servicing node that receives the action.

13. The system as in claim 1, wherein the performing of at least partial execution of the action by the servicing node comprises generating a supplementary action and transmitting the supplementary action to a second servicing node, the second servicing node using the supplementary action to generate additional results comprising the customized service.

14. The system as in claim 1, wherein at least a part of the customized service identified by the Object ID is provided by a service device separate from the originating device.

15. The system as in claim 14, wherein the performing of at least partial execution of the action by the servicing node to generate results includes generating control commands based on the received action and transmitting the control commands to the service device, the control commands provided to the service device corresponding to the customized service provided.

* * * * *